United States Patent [19]

Erickson

[11] 4,155,360
[45] May 22, 1979

[54] DEVICE TO MINIMIZE PUBIC AREA IRRITATION FOLLOWING SURGERY

[76] Inventor: George A. Erickson, Rte. 1, Box 173, Dundee, Minn. 56126

[21] Appl. No.: 823,925

[22] Filed: Aug. 12, 1977

[51] Int. Cl.² ............................................. A61B 19/00
[52] U.S. Cl. .................................... 128/149; 128/577
[58] Field of Search ................... 128/149, 577, 132 R, 128/158, 159, 288, 526, 154, 289; 2/46

[56] References Cited

U.S. PATENT DOCUMENTS

| 995,600 | 6/1911 | Heyser | 128/158 |
| 1,641,568 | 9/1927 | Roano | 128/149 |
| 1,865,280 | 6/1932 | Risley | 128/138 |
| 2,283,684 | 5/1942 | Matthews | 128/160 |
| 2,831,486 | 4/1958 | Sanders | 128/289 |
| 2,854,973 | 10/1958 | Jackson | 128/149 |
| 2,943,623 | 7/1960 | Thompson | 128/149 |
| 3,176,686 | 4/1965 | Barnes | 128/132 R |
| 3,229,692 | 1/1966 | Creed | 128/158 |
| 3,314,422 | 4/1967 | Phillips | 128/132 R |
| 3,518,995 | 7/1970 | Claff | 128/379 |

FOREIGN PATENT DOCUMENTS

| 613611 | 8/1926 | France | 128/158 |
| 1003779 | 11/1951 | France | 128/158 |

Primary Examiner—Lawrence W. Trapp
Attorney, Agent, or Firm—Merchant, Gould, Smith, Edell, Welter & Schmidt

[57] ABSTRACT

A method and apparatus for reducing itching of shaven, normally hirsute body portions during the period of hair regrowth. A lamina of flexible, smooth, non-woven material such as plastic is secured to the inner surface of the user's undergarment so that hair ends may move freely with respect to the surface rather than being trapped thereby.

1 Claim, 6 Drawing Figures

DEVICE TO MINIMIZE PUBIC AREA IRRITATION FOLLOWING SURGERY

BACKGROUND OF THE INVENTION

This invention relates to the field of medicine, and particularly to an arrangement and method for ameliorating the annoyance of itching, at hirsute areas shaven for medical reasons, during the period of regrowth of hair in the shaven areas.

It is standard hospital procedure to shave the pubic area prior to surgical procedures, including delivery, for example. During the early post-operative or post-partal period, the patients frequently complain of severe itching of the shaven area caused by engagement of the ends of the emerging short hairs with the patient's undergarments.

SUMMARY OF THE INVENTION

This invention minimizes the unwelcome itching by interposing between the body area in question and the patient's undergarments a lamina of smooth, flexible, non-woven material such as plastic having a surface with a sufficiently hard finish to be slippery and hence not prevent relative movement of the hair ends, while being supple enough to conform to the body contours of the patient. The lamina is secured within an undergarment, and covers only the shaven area, to minimize sweating.

Various advantages and features of novelty which characterize my invention are pointed out with particularity in the claims annexed hereto and forming a part hereof. However, for a better understanding of the invention, its advantages, and objects attained by its use, reference should be had to the drawing which forms a further part hereof, and to the accompanying descriptive matter, in which there are illustrated and described certain preferred embodiments of the invention.

DESCRIPTION OF THE PREFERRED EMBODIMENT

Figure 1:
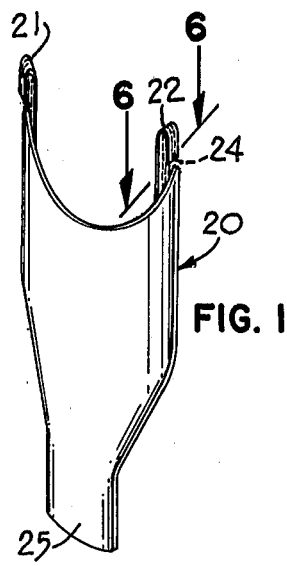
FIG. 1 is a perspective view of one embodiment of the invention.
Figure 2:
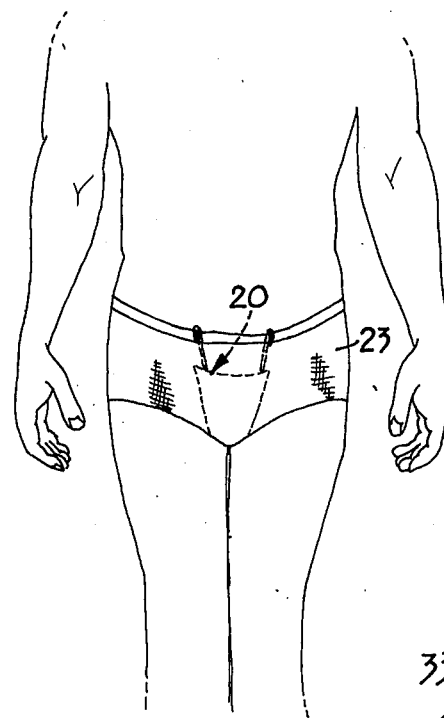
FIG. 2 is illustrative of this embodiment in use.
Figure 6:
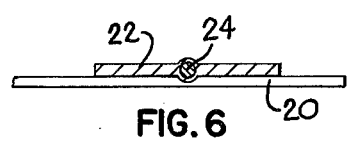
FIG. 6 is a sectional view along the line 6—6 of FIG. 1.

As shown in FIG. 1, my invention comprises a sheet or lamina 20 of flexible, hard surface plastic which is generally V-shaped. It is provided with tabs or loops 21, 22 for securing its wide end to the waistband of an undergarment 23, as shown in FIG. 2: attachment to the body of the patient is not intended. For convenience, the tabs may be provided with soft metal wires or strips as shown at 24 in FIG. 6. The structure is dimensioned in accordance with the pubic and perineal area of patients generally, but is intended to be trimmed with scissors to cover only the shaven area for each particular patient, to minimize the patient's discomfort due to sweating. An extension 25 is provided to pass between the patient's legs, but is intended to be cut off so that only so much area remains covered as is necessary in each particular case. The purpose of the lamina is to provide a surface next to the patient's body which is smooth and relatively slippery, so that the ends of regrowing hairs may move freely across it rather than being entrapped in the interstices of a fabric and thus irritate the skin of the wearer.

Any plastic can be used for this purpose which is capable of being formed into a flexible sheet or lamina having a surface hard enough that hair ends do not penetrate it, but rather slide freely across it. By way of illustration and not limitation, I suggest vinyl or vinylidene plastics, urethanes, polyesters, and silicone rubbers for this purpose.

Figure 3:
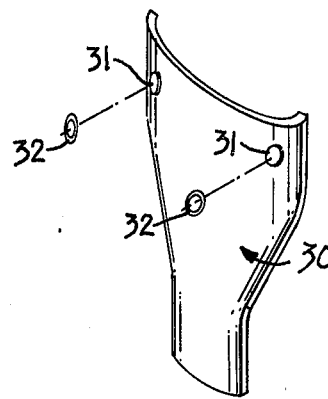
FIG. 3 is a perspective view of the second embodiment of the invention.
Figure 5:
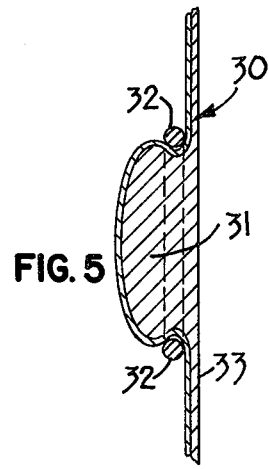
FIG. 5 is a fragmentary sectional view along the line 5—5 of FIG. 4.
Figure 4:
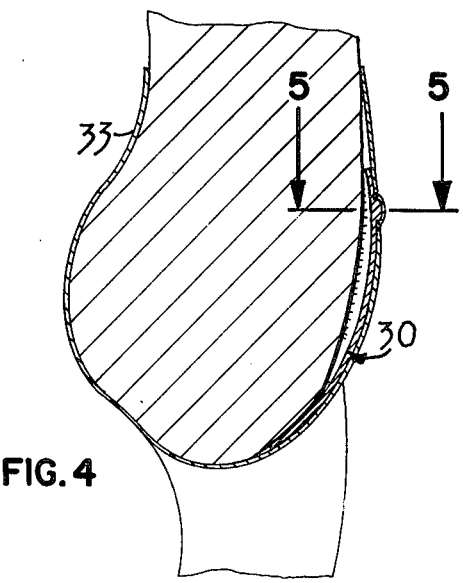
FIG. 4 is a sectional view showing this embodiment in use.

A second embodiment of the invention is shown in FIG. 3 to comprise as before a sheet or lamina 30, but this time without loops or ties. Instead, the plastic of the lamina is thickened to form two buttons 31 having reentrant edges. A pair of O-rings 32 are provided to secure the shield to an undergarment 33 as is shown generally in FIG. 4 and in detail in FIG. 5.

From the foregoing, it will be evident that I have invented a method of and apparatus for minimizing post-operative itching by interposing between the shaven surface and the patient's undergarment a lamina of flexible smooth plastic having a hard or slippery surface such that the newly grown hair ends can move freely therealong instead of being trapped thereby.

Numerous characteristics and advantages of my invention have been set forth in the foregoing description, together with details of the structure and function of the invention, and the novel features thereof are pointed out in the appended claims. The disclosure, however, is illustrative only, and changes may be made in detail especially in matters of shape, size, and arrangement of parts, within the principle of the invention, to the full extent indicated by the broad general meaning of the terms in which the appended claims are expressed.

I claim:

1. Apparatus for reducing itching of shaven, normally hirsute body portions during a period of hair regrowth which comprises a lamina of smooth, flexible, non-woven material positioned between the shaven body portion and the adjacent garment to prevent engagement of the regrowing hair with fabric interstices, said lamina having the general configuration of an isosceles triangle with its apex directed downwardly, and including tabs with soft metal inserts therein at the base angles thereof for connecting it inside the waistband of an undergarment.

* * * * *